(12) United States Patent
Damaj

(10) Patent No.: US 10,500,199 B2
(45) Date of Patent: Dec. 10, 2019

(54) NUTRITIONAL SUPPLEMENT FOR INCREASING COGNITIVE FUNCTIONS

(71) Applicant: Innovus Pharmaceuticals, Inc., San Diego, CA (US)

(72) Inventor: Bassam Damaj, San Diego, CA (US)

(73) Assignee: Innovus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/829,801

(22) Filed: Dec. 1, 2017

(65) Prior Publication Data

US 2019/0167656 A1 Jun. 6, 2019

(51) Int. Cl.
| | | |
|---|---|---|
| *A61K 31/4525* | (2006.01) | |
| *A23L 33/175* | (2016.01) | |
| *A61P 25/28* | (2006.01) | |
| *A61K 31/198* | (2006.01) | |

(52) U.S. Cl.
CPC ........ *A61K 31/4525* (2013.01); *A23L 33/175* (2016.08); *A61K 31/198* (2013.01); *A61P 25/28* (2018.01)

(58) Field of Classification Search
CPC .......................... C07D 413/14; A61K 31/4525
See application file for complete search history.

(56) References Cited

U.S. PATENT DOCUMENTS

| | | | |
|---|---|---|---|
| 5,536,506 A * | 7/1996 | Majeed .................. | A61K 47/22 424/423 |
| 5,744,161 A | 4/1998 | Majeed et al. | |
| 7,262,192 B2 | 8/2007 | Bell et al. | |
| 9,161,565 B1 | 10/2015 | Bezzek | |
| 2001/0008641 A1 | 7/2001 | Krotzer | |
| 2008/0305096 A1 | 12/2008 | Verdegem et al. | |
| 2009/0143433 A1* | 6/2009 | Hendrix .................. | A61K 9/06 514/321 |
| 2016/0106793 A1* | 4/2016 | Peltier .................. | A23L 33/105 424/93.4 |

FOREIGN PATENT DOCUMENTS

| | | |
|---|---|---|
| EP | 0810868 B1 | 8/2001 |
| EP | 2027857 A2 | 2/2009 |
| WO | 2015048590 A1 | 4/2015 |
| WO | 2015061860 A1 | 5/2015 |

OTHER PUBLICATIONS

Alexandra et al., PLoS One, 2013, 8(7), e67707.*
Morris, The Journal of Nutrition, 2004, 134 (10 Suppl): 2743S-2747S, discussion 2765S-2767S.*
Arginine/citrulline complex capsules from Puritan's Pride, 2013.*
Manukhina et al. Bulletin of Experimental Biology and Medicine, 2008, 146(4):391-395.*
Fry et al. Am J. Physiol Renal Physiol, 2016, 310(3): F237-47.*
Mehmood, et al., "Black Pepper and Pipeline Possess Antidiarrheal Effect Mediated Through Phosphodiesterase Inhibitory and CA++ Antagonist Pathways", Basic & Clinical Pharmacology & Toxicology 1 (Suppl 1) Abstract # 834, 256 (2014).
Niuliv Science, "ASTRAGIN", Product Insert pdf, www.nulivscience.com, 2 pages (2018).
Niuliv Science, "NUTRA", http://www.nutraingredients-usa.com/articles/2012/03/26nuliv-science-annouces-self-affirmed-GRAS-for-AstraGin-ingredient, 2 pages (2012).
Recalmax, Product Insert, Innovus Pharmaceuticals, Inc., 3 pages (Oct. 2016).
Vesele, Product Insert, Innovus Pharmaceuticals, Inc., 3 pages (Oct. 2016).
Awad, et al., "Effect of beta-sitosterol, a plant sterol, on growth, protein phosphatase 2A, and phospholipase D in LNCaP cells", Nutr Cancer 36(1), 74-78 (2000) Abstract, 2 pages.
CAS Registry, RN 94-62-2, Listing for Piperine, 1 page, (1984).
Life Extension, "All About Supplements—Pygeum", http://222.lifeextension.com/magazine/2006/4/aas/page-01, 5 pages, retrieved on Sep. 24, 2018.
Mascio, et al., "Lycopene as the most efficient biological carotenoid singlet oxygen quencher", Archives of Biochemistry and Biophysics 274(2), 532-538 (1989). Abstract, 2 pages.
Mukhtar, et al., "Green Tea in Chemoprevention of Cancer", Toxicological Sciences 52 (Supplement), 111-117 (1999).
Perva-Uzunalic, et al., "Extraction of active ingredients from green tea (*Camellia sinensis*): Extraction efficiency of major catechins and caffeine", Food Chemistry 96, 597-605 (2006).
Riehemann, et al., "Plant extracts from stinging nettle (*Urtica dioica*), an antirheumatic remedy, inhibit the proinflammatory transcription factor NF-kB", FEBS Letters 442, 89-94 (1999).
U.S. Non-Final Office Action, for U.S. Appl. No. 15/829,822, 9 pages, dated Sep. 20, 2018.
WEBMD, "Saw Palmetto", https://www.webmd.com/vitamins/ai/ingredientmono-971/saw-palmetto, 4 pages, retrieved on Sep. 24, 2018.
U.S. Appl. No. 15/829,799.
U.S. Appl. No. 15/829,798.
U.S. Appl. No. 15/829,797.
U.S. Appl. No. 15/829,822.

* cited by examiner

*Primary Examiner* — Rei Tsang Shiao
(74) *Attorney, Agent, or Firm* — Viksnins Harris Padys Malen LLP

(57) ABSTRACT

The invention provides compositions and methods that are effective to improve NO production in vivo and/or to increase NO levels in blood. Such compositions and methods are useful to increase oxygenation of the brain and to improve cognitive function.

19 Claims, 3 Drawing Sheets

Piperine Structure (2E,4E)-5-(benzo[d][1,3]dioxol-5-yl)-1-(piperidin-1-yl)penta-2,4-dien-1-one

NUTRITIONAL SUPPLEMENT FOR INCREASING COGNITIVE FUNCTIONS

BACKGROUND OF THE INVENTION

Nitric Oxide Synthase (NOS) in endothelial cells converts L-arginine to L-hydroxyarginine and subsequently to nitric oxide (NO) and L-citrulline (FIG. 1 and FIG. 2). NO exerts its biological action on smooth muscle by increasing cGMP, which leads to vasodialation and increased blood flow in the brain. Two L-citrulline molecules combine to generate L-arginine to boost the NO generation cycle. NO acts as a neurotransmitter for the autonomic nervous system, increases cerebral blood flow and oxygenation of the brain, and improves cognitive functions.

A previous dietary supplement was designed and sold to maximize the benefits of NO. It contained the amino acids L-citruline and L-arginine, as well as BioPerine® (extract, FIG. 3) that helps the body absorb the amino acids (see U.S. Pat. No. 5,536,506 and European Patent EP0810868B1). BioPerine® (extract) inhibits human CYP3A4 and P-glycoprotein enzymes. By inhibiting certain enzymes BioPerine® (extract) may alter the effectiveness of certain medications by increasing bioavailability. The active ingredients in this previous dietary supplement were the amino acids L-citruline and L-arginine, which served as a substrate for NO generation. The previous dietary supplement was sold and administered as a capsule containing 500 mg of L-citrulline, 250 mg of L-arginine, and 1.5 mg of bioperine. The recommended dosage was two capsules per day. In spite of the success realized with the previous dietary supplement, there remains a need for additional formulations that provide improved effects.

SUMMARY OF THE INVENTION

Applicant has determined that the beneficial effects of the previous dietary supplement can be significantly improved by increasing the amount of piperine in the formulation from 1.5 mg to about 5 mg. Based on the suggested administration of two capsules per day, this represents an increase in the amount of piperine from 3.0 mg to about 10.0 mg per day.

Accordingly, in one embodiment the invention provides a unit dosage form suitable for oral administration to a human comprising: L-citrulline (500 mg±20 mg); L-arginine (250 mg±20 mg); and at least about 5 mg piperine.

In another embodiment the invention provides a unit dosage form suitable for oral administration to a human comprising: about 500 mg of L-citrulline; about 250 mg of L-arginine; and about 5 mg of bioperine.

In another embodiment the invention provides a method to increase NO levels in the blood of a mammal comprising administering a unit dosage form of the invention to the mammal.

In another embodiment the invention provides a method to increase cerebral blood flow in a mammal comprising administering a unit dosage form of the invention to the mammal.

In another embodiment the invention provides a method to increase oxygenation of the brain in a mammal comprising administering a unit dosage form of the invention to the mammal.

In another embodiment the invention provides a method to improve cognitive function in a mammal comprising administering a unit dosage form of the invention to the mammal.

DETAILED DESCRIPTION

Figure 1:
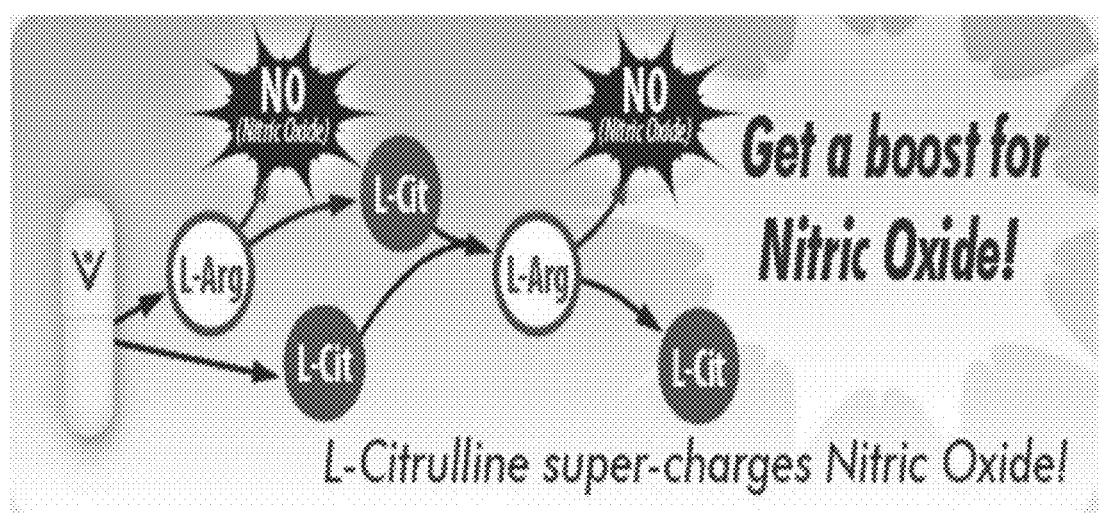
FIG. 1 shows the conversion of L-citrulline and L-arginine to NO.
Figure 2:
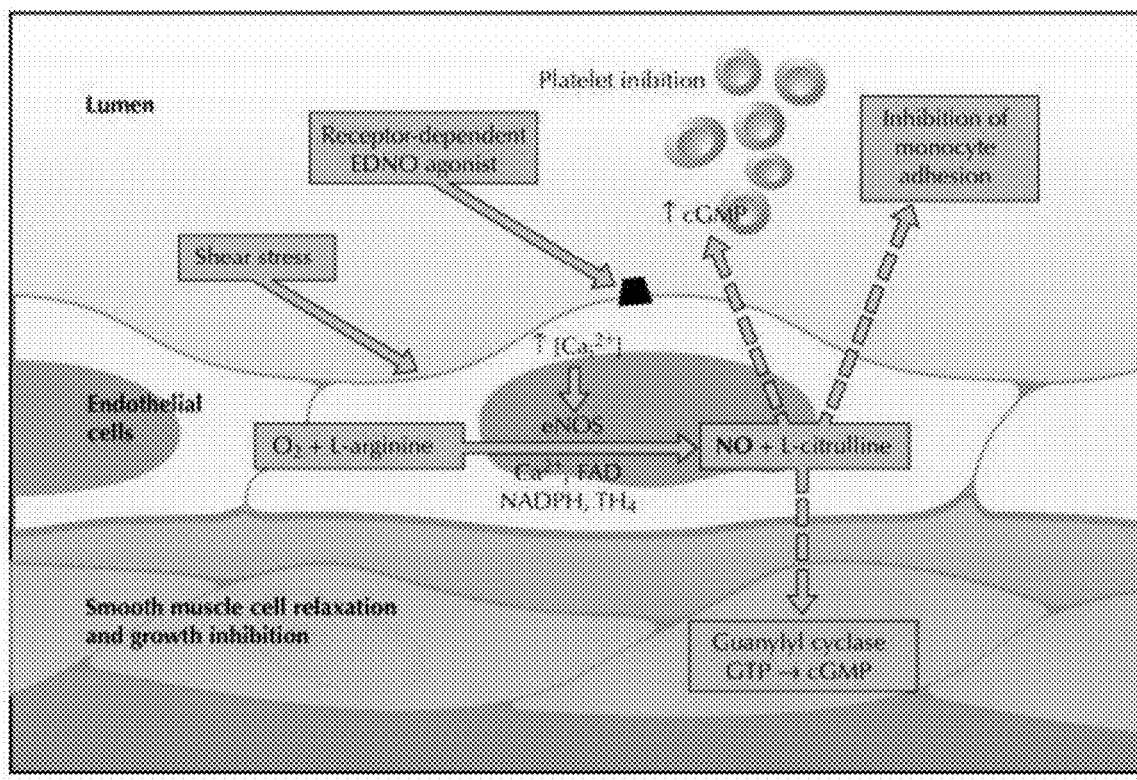
FIG. 2 shows how Nitric Oxide Synthase (NOS) in endothelial cells converts L-arginine to L-hydroxyarginine and subsequently to nitric oxide (NO) and L-citrulline.
Figure 3:
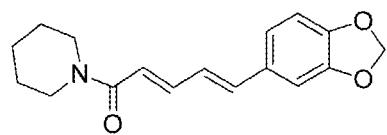
FIG. 3 shows the structure for piperine.

As used herein, the term "about" has its generally accepted meaning. In one embodiment, the term about means±10% of the associated value. For example, about 100 mg means 100 mg±10 mg. In one embodiment, the term about means±5% of the associated value. For example, about 100 mg means 100 mg±5 mg. In one embodiment, the term about means±2% of the associated value. For example, about 100 mg means 100 mg±2 mg. In one embodiment, the term about means±1% of the associated value. For example, about 100 mg means 100 mg±1 mg.

In one embodiment a unit dosage form of the invention may contain one or more pharmaceutical diluents or excipients. For example, in one embodiment a unit dosage form of the invention may comprise microcrystalline cellulose, silicon dioxide, and magnesium stearate.

In one embodiment a unit dosage form of the invention may comprise at least about 480 mg of L-citrulline.

In one embodiment a unit dosage form of the invention may comprise at least about 490 mg of L-citrulline.

In one embodiment a unit dosage form of the invention may comprise at least about 500 mg of L-citrulline.

In one embodiment a unit dosage form of the invention may comprise at least about 230 mg of L-arginine.

In one embodiment a unit dosage form of the invention may comprise at least about 240 mg of L-arginine.

In one embodiment a unit dosage form of the invention may comprise at least about 250 mg of L-arginine.

In one embodiment the piperine is synthetically produced piperine.

In one embodiment the piperine is an extract from the fruit of Piper.

L-Argenine is an α-amino acid that is used in the biosynthesis of proteins. It is the precursor for the biosynthesis of nitric oxide. L-Argenine has the following structure:

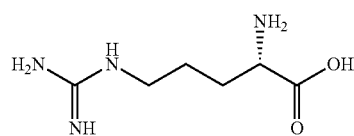 [SMILES: N=C(N)NCCC[C@H](N)C(=O)O]

In humans, arginine is classified as a semiessential or conditionally essential amino acid, depending on the developmental stage and health status of the individual. L-Argenine is commercially available from a variety of sources.

L-Citrulline is an α-amino acid that is a key intermediate in the urea cycle, the pathway by which mammals excrete ammonia by converting it into urea. Citrulline is also produced as a byproduct of the enzymatic production of nitric oxide from the amino acid arginine, catalyzed by nitric oxide synthase. L-Citrulline has the following structure:

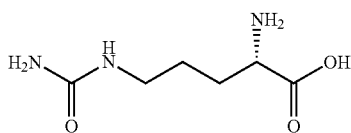

L-Citrulline is commercially available from a variety of sources.

Bioperine® is a patented absorption enhancer, obtained from black pepper fruits (*Piper nigrum*). Bioperine® helps the body absorb the amino acids (see U.S. Pat. No. 5,536,506 and European Patent EP0810868B1). Bioperine® (extract) inhibits human CYP3A4 and P-glycoprotein enzymes. By inhibiting certain enzymes Bioperine® (extract) may alter the effectiveness of certain medications by increasing bioavailability. Bioperine is Generally Recognized As Safe (GRAS). Bioperine® (CAS Reg. No. 94-62-2) is named as 1-piperylpiperidine; 5-(1,3-benzodioxol-5-yl)-1-(piperidin-1-yl)penta-2,4-dien-1-one; and (2E,4E)-5-(1,3-benzodioxol-5-yl)-1-(piperidin-1-yl)penta-2,4-dien-1-one, and has the structure:

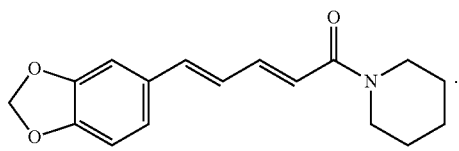 [SMILES: O=C(/C=C/C=C/c1ccc2c(c1)OCO2)N1CCCCC1]

1-Piperylpiperidine is commercially available from a variety of sources.

The invention will now be illustrated by the following non-limiting Examples.

EXAMPLE 1

The chart below describes the changes between the old formulation and the present invention based on the satisfaction rate for the customer's processing fees. The new formulation shows a 19.9 percent increase processing speed over four months as opposed to the old formulation with only as 2.9 percent increase in processing speed.

|  | Old Formulation Satisfaction Rate | Present Invention Satisfaction Rate |
| --- | --- | --- |
| Baseline | 688 | 59 |
| At 4 Month | 62.3 | 78.9 |
| % Increase | 2.9 | 19.9 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A unit dosage form suitable for oral administration to a human comprising:
   L-citrulline 500 mg±20 mg;
   L-arginine 250 mg±20 mg; and
   at least about 5 mg piperine.
2. The unit dosage form of claim 1 that comprises at least about 5.0 mg piperine.
3. The unit dosage form of claim 1 that comprises at least about 5.3 mg piperine.
4. The unit dosage form of claim 1 that comprises at least about 5.5 mg piperine.
5. The unit dosage form of claim 1 that further comprises microcrystalline cellulose, silicon dioxide, and magnesium stearate.
6. The unit dosage form of claim 1 that comprises at least about 480 mg of L-citrulline.
7. The unit dosage form of claim 1 that comprises at least about 490 mg of L-citrulline.
8. The unit dosage form of claim 1 that comprises at least about 500 mg of L-citrulline.
9. The unit dosage form of claim 1 that comprises at least about 230 mg of L-arginine.
10. The unit dosage form of claim 1 that comprises at least about 240 mg of L-arginine.
11. The unit dosage form of claim 1 that comprises at least about 250 mg of L-arginine.
12. The unit dosage form of claim 1 that comprises:
    about 500 mg of L-citrulline;
    about 250 mg of L-arginine; and
    about 5 mg of (2E,4E)-5-(1,3-benzodioxol-5-yl)-1-(piperidin-1-yl)penta-2,4-dien-1-one.
13. The unit dosage form of claim 1 wherein the piperine is synthetically produced piperine.
14. The unit dosage form of claim 1 wherein the piperine is an extract from the fruit of Piper.
15. The unit dosage form of claim 12 that further comprises microcrystalline cellulose, silicon dioxide, and magnesium sterate.
16. The unit dosage form of claim 1 that is formulated as a capsule, powder, or liquid.
17. A method to increase NO levels in the blood of a mammal comprising administering a unit dosage form of claim 1 to the mammal.
18. A method to increase oxygenation of the brain in a mammal comprising administering a unit dosage form of claim 1 to the mammal.
19. A method to improve cognitive function in a mammal comprising administering a unit dosage form of claim 1 to the mammal.

* * * * *